(12) United States Patent
Miller et al.

(10) Patent No.: US 6,801,804 B2
(45) Date of Patent: Oct. 5, 2004

(54) DEVICE AND METHOD FOR MONITORING AND CONTROLLING ELECTRICAL RESISTANCE AT A TISSUE SITE UNDERGOING IONTOPHORESIS

(75) Inventors: David J. Miller, Bountiful, UT (US); William I. Higuchi, Salt Lake City, UT (US); Kevin Li, Salt Lake City, UT (US); Matthew S. Hastings, Sandy, UT (US)

(73) Assignee: Aciont, Inc., Salt Lake City, UT (US)

( * ) Notice: Subject to any disclaimer, the term of this patent is extended or adjusted under 35 U.S.C. 154(b) by 335 days.

(21) Appl. No.: 10/138,723

(22) Filed: May 3, 2002

(65) Prior Publication Data

US 2003/0208235 A1 Nov. 6, 2003

(51) Int. Cl.[7] .................................................. A61N 1/30
(52) U.S. Cl. ...................................................... 604/20
(58) Field of Search ....................... 604/20–21; 607/153

(56) References Cited

U.S. PATENT DOCUMENTS

| | | | |
|---|---|---|---|
| 4,141,359 A | | 2/1979 | Jacobsen et al. |
| 5,246,418 A | | 9/1993 | Haynes et al. |
| 5,415,629 A | | 5/1995 | Henley |
| 5,771,890 A | | 6/1998 | Tamada |
| 5,954,685 A | * | 9/1999 | Tierney ........................ 604/20 |
| 5,983,134 A | * | 11/1999 | Ostrow ........................ 604/20 |
| 6,139,718 A | | 10/2000 | Kurnik et al. |
| 6,144,869 A | | 11/2000 | Berner et al. |
| 6,180,416 B1 | | 1/2001 | Kurnik et al. |
| 6,201,979 B1 | | 3/2001 | Kurnik et al. |
| 6,233,471 B1 | | 5/2001 | Berner et al. |
| 6,248,349 B1 | | 6/2001 | Suzuki et al. |
| 6,259,946 B1 | | 7/2001 | Higo et al. |
| 6,284,126 B1 | | 9/2001 | Kurnik et al. |
| 6,326,160 B1 | | 12/2001 | Dunn et al. |
| 6,496,728 B2 | * | 12/2002 | Li et al. ........................ 604/20 |
| 6,512,950 B2 | * | 1/2003 | Li et al. ........................ 604/20 |

FOREIGN PATENT DOCUMENTS

| WO | WO 01/60448 | 8/2001 |
|---|---|---|
| WO | WO 01/60449 | 8/2001 |

* cited by examiner

Primary Examiner—Mark Bockelman
(74) Attorney, Agent, or Firm—Reed & Eberle LLP (57) ABSTRACT

The invention provides a device for iontophoretically transporting a compound through a localized region of an individual's body tissue. The device comprises first and second iontophoretic electrodes, a reference electrode, a current source, and a monitoring means. The first electrode is placed in ion-conducting relation with the localized region to allow iontophoretic transport of a compound therethrough. The second and transport electrodes are each placed in contact with the individual's body tissue, and all electrodes are spaced apart from each other. The current source is electrically connected to the first and second electrodes and applies a current to the localized region of body tissue to effect iontophoretic transport. The monitoring means monitors the electrical resistance of the localized region by measuring any voltage difference between the reference electrode and the first and/or second electrodes. Methods for using a reference electrode to monitor and control iontophoresis are also provided.

64 Claims, 3 Drawing Sheets

DEVICE AND METHOD FOR MONITORING AND CONTROLLING ELECTRICAL RESISTANCE AT A TISSUE SITE UNDERGOING IONTOPHORESIS

TECHNICAL FIELD

The invention relates generally to a device and method for monitoring and controlling the iontophoretic transport of a compound through a localized region of an individual's body tissue. In particular, the invention employs a novel reference electrode, in conjunction with at least one of two iontophoretic electrodes, to monitor and control the electrical resistance of the tissue at the localized region. The invention is particularly useful when there is a need to precisely control the administration of a compound to, or the extraction of a compound from a body tissue, such as in the administration or monitoring of a therapeutic drug or glucose, for example.

BACKGROUND

Iontophoresis involves the transport of a compound across a body tissue under the influence of an electrical current. In practice, two iontophoretic electrodes are placed on a body tissue, typically the skin or mucosa, in order to complete a circuit. At least one of the electrodes is considered to be an active iontophoretic electrode, while the other may be considered as a return, inactive, or indifferent electrode. Compound transport across the tissue occurs when a current is applied to the electrodes through the tissue. Compound transport may occur as a result of a direct electrical field effect (e.g., electrophoresis), an indirect electrical field effect (e.g., electroosmosis), electrically induced pore formation (electroporation), or a combination of any of the foregoing.

Iontophoretic techniques have been used to deliver compounds to, or extract compounds from, body tissues of a patient. When iontophoresis is used to deliver a compound to the tissue, an active iontophoretic electrode is provided with a reservoir containing the compound to be delivered, as well as optional additional compounds that may serve to enhance iontophoretic delivery. For example, U.S. Pat. No. 6,248,349 to Suzuki et al. describes an iontophoretic electrode in combination with an interface capable of making contact with the skin that effectively holds a drug and humectant mixture. The humectant is described as improving iontophoretic drug delivery by controlling the concentration of the drug at the delivery site. Similarly, when iontophoresis is used to extract a compound from the tissue, the active iontophoretic electrode may be provided with a reservoir for collecting the extracted compound. Further, additional compounds may be added to the receiving reservoir to enhance iontophoretic extraction. Once extracted, the compound may be analyzed using sensors, processors, and algorithms known in the art. See U.S. Pat. Nos. 6,139,1718; 6,144,869; 6,180,416; 6,201,979; 6,233,471; 6,284,126; and 6,326,160.

In some instances, the process of iontophoresis can cause irritation, sensitization, and pain at the application site. The effects of the electrical current on sensitization have been investigated in various attempts to develop iontophoretic methods that are capable of maintaining the electrical current and/or potential at a comfortable level. It has been found that the degree of irritation, sensitization, and/or pain is directly proportional to the applied current or voltage. Thus, there is a need to apply iontophoretic current at a level that is effective to transport compounds of interest at a desired rate but that does not cause tissue irritation, sensitization, and/or pain.

A majority of the known iontophoretic methods employ a constant direct current (DC) iontophoretic signal and suffer from a number of shortcomings as a consequence. It is generally believed that the constant driving force provided by the DC current will produce a constant, unwavering permeant flux. It has been observed, however, that a constant current DC signal does not result in constant flux. The constant DC causes the electrical resistance of the tissue to change as a result of variations in tissue porosity, pore surface charge density, and effective pore size over the course of treatment. As a result, the amount of compound transported across a tissue varies with time and cannot be controlled, monitored, or predicted effectively. The inability to control analyte flux during iontophoresis has proven to be a major constraint to the marketing and regulatory success of iontophoretic products.

In addition, iontophoretic techniques that employ a constant DC signal can result in the formation of unwanted byproducts. For example, the application of a constant direct current to a tissue can result in water hydrolysis at the treatment site, causing protons to accumulate at the anode and hydroxide ions to accumulate at the cathode. The resulting shift in pH at the electrodes may cause tissue irritation and/or damage. In extreme cases, this resulting electrolysis causes gas formation at the interface between the active electrode and tissue in contact with it. As a consequence, interfacial electrical resistance may be altered as well. The highly mobile hydrogen and hydroxide ion byproducts of water hydrolysis competes against the permeant for the electrical current, thereby decreasing permeant transport efficiencies.

As a whole, the overarching problem associated with DC iontophoretic systems is their high degree of variability. A number of attempts have been made to overcome the problems associated with constant DC signals by using pulsed DC signals and signals of different waveforms. In theory, pulsed DC signals improve iontophoretic delivery by allowing skin capacitance to discharge, thereby dissipating accumulative pore charging and the resulting formation of electropotential barriers. This capacitance discharge is thought to permit more controlled current flow and agent transport. In some instances, employing pulsed DC signals may involve switching the polarity of electrodes between the pulses. See U.S. Pat. No. 5,771,890 to Tamada. In practice, however, many DC pulsed methods suffer from at least some of the same general drawbacks as the constant current DC methods.

Iontophoretic methods that use alternating current (AC) signals, with or without a DC offset, have exhibited improved performance for both compound delivery and extraction. The premise of AC constant conductance iontophoresis is that molecular transport across a tissue is directly proportional to the tissue's conductivity and inversely related to the tissue's resistivity. The conductance of the membrane is a direct measure of the ease of passage of molecules and ions, but in particular, sodium and chloride ions. It has been found that, at constant current levels, the molecular transport though a membrane is related to the conductance of the membrane. AC iontophoretic methods are described in U.S. patent application Ser. No. 09/783,138, entitled "Methods for Delivering Agents Using Alternating Current," filed on Feb. 13, 2001, corresponding to International Patent Publication No. WO 01/60449. AC iontophoretic methods are also described in U.S. patent application Ser. No. 09/783,696, entitled "Methods for Extracting Substances Using Alternating Current," filed on Feb. 13, 2001, corresponding to International Patent Publication No. WO 01/60448.

In order to reduce the energy requirements needed to effect iontophoretic transport, it has been discovered that application of a barrier-modifying substance (also referred to herein as a "barrier-modifying agent" or "barrier modifier") to the body tissue, either prior to or during AC iontophoresis, lowers the potential voltage difference needed to achieve electroporation. As discussed in U.S. patent application Ser. No. 10/014,741, entitled "Method of Increasing the Battery Life of an Alternating Current Iontophoresis Device Using a Barrier-Modifying Agent," filed on Dec. 10, 2001, the use of such barrier modifiers makes it possible to maintain the rate at which a compound of interest can be transported through a body tissue at lower electrical voltage levels. This reduction in applied voltage ultimately results in increased battery life, extended treatment duration, decreased treatment cost, and increased patient comfort.

In order to optimize iontophoretic methods, there is a need to monitor the amount of current being applied to the tissue of interest, as well as the transport of the specific compound through the tissue. A number of techniques have been developed to monitor iontophoretic current. For example, U.S. Pat. No. 5,246,418 to Haynes et al. discloses a method of reducing irritation during iontophoresis using a circuit that provides electrical communication between the iontophoretic electrodes. In essence, the circuit monitors and controls the current passing through the electrodes and the tissue. Similarly, U.S. Pat. No. 4,141,359 to Jacobsen et al. describes an epidermal iontophoresis device that includes an impedance-checking circuit coupled to the iontophoretic electrodes, and a safety-shutdown circuit coupled to the impedance-checking circuit that prevents an excessive voltage differential from being applied across the electrodes.

In previous methods for measuring electrical resistance associated with iontophoresis, it has been assumed that the resistance measured across the iontophoretic electrodes is evenly distributed across the two sites. For example, it was assumed that a measured resistance of 10 k$\Omega$ across the electrodes of an iontophoretic system indicated that the resistance at each electrode was 5 k$\Omega$. It has recently been discovered, however, that electrical resistance at the iontophoretic electrodes may change independently from each other during iontophoresis. In many cases, a constant measured resistance between two electrodes results from an increasing resistance at one electrode and a decreasing resistance at the other electrode. Thus, there is a need in the art to monitor the electrical resistance and control the electrical parameters at iontophoretic electrodes independently from each other in order to improve iontophoretic transport precision.

SUMMARY OF THE INVENTION

In a first embodiment, the invention relates to a device for iontophoretically transporting a compound through a localized region of an individual's body tissue. The device includes first and second iontophoretic electrodes, a reference electrode, a current source, and a monitoring means. The first electrode is adapted to be placed in ion-conducting relation with the localized region to allow iontophoretic transport of a compound therethrough. The second and reference electrode are each adapted to contact the individual's body tissue, and all electrodes are spaced apart from each other. Optionally, the second and/or the reference electrodes are adapted to be placed in ion-conducting relation with the body tissue as well. The current source is electrically connected to the first and second electrodes and is capable of applying an AC or DC current to the localized region of body tissue to effect iontophoretic transport of the compound through the localized region. The monitoring means monitors the electrical resistance of the localized region by measuring any voltage difference between the reference electrode and at least one of the first and second electrodes. To ensure accurate monitoring of the resistance of the localized region, the reference electrode is typically immobilized with respect to at least one of the first and second electrodes.

Preferably, the inventive device employs a controller. The controller may control the current or voltage applied to the localized region of body tissue by the current source. The controller may also control the duration of current and/or voltage application. Typically, the controller is adapted to control the current applied to the localized region according the electrical resistance of the localized region as monitored by the monitoring means. A feedback mechanism may be employed, wherein the controller is adapted to control the current applied to the localized region to maintain the electrical resistance of the localized region within a predetermined resistance range. Optimally, the controller maintains the resistance of the tissue in contact with the first electrode and the reference electrode at a constant value.

When the device is adapted to transport a compound into the localized region, the first electrode may be constructed as a component of an electrode assembly adapted to deliver the compound through the localized region. In such cases, the assembly may include a reservoir that houses the compound, e.g., a pharmacologically active agent. When the device is adapted to extract a compound from the localized region, the first electrode may be constructed as a component of an electrode assembly adapted to receive a compound transported through the localized region. In such cases, the assembly may house a reservoir for collecting and containing the extracted compound. In either case, the assembly may also include a barrier-modifying agent that may be delivered to the localized region. Typically, barrier-modifying agents are permeation enhancers.

Optionally, the inventive device may include a sensor in the reservoir for measuring the quantity and/or concentration of the compound to be delivered to, or extracted from, the localized region. The sensor may operate according to any known sensing technique. For example, the sensor may be an electrochemical sensor comprised of a working electrode, a counter electrode, and an optional sensor reference electrode. Typically, but not necessarily, the sensor reference electrode does not also serve as the reference electrode used in monitoring the electrical resistance of the localized region, as discussed above. The sensor, for example, may be a coulometric, amperometric, or potentiometric sensor. Similarly, the sensor may be an optical sensor.

The monitoring means may be adapted to continuously or intermittently monitor the electrical resistance of the localized region. Ordinarily, intermittent monitoring involves monitoring at a predetermined regular interval occurring at a constant frequency. However, the predetermined intervals may occur at an increasing or decreasing frequency as well. In some instances, the monitoring means is adapted to monitor the electrical resistance of the localized region at intervals selected according to the electrical potential applied by an iontophoretic power supply that serves as the current source.

In another embodiment, the invention relates to a method for iontophoretically transporting a compound through a localized region of an individual's body tissue. The method involves placing a first electrode in ion-conducting relation with the localized region and placing second and reference electrodes in contact with the individual's body tissue. Once the electrodes are in appropriate positions, i.e., placed apart from each other, a current is applied to the localized region of body tissue through the first and second electrodes to effect iontophoretic transport of a compound through the localized region. While the current is applied, the electrical resistance of the localized region is monitored. This method can be carried out by measuring any voltage difference between the reference electrode and at least one of the first and second electrodes.

Optionally, the inventive method is carried out using the inventive device. While the invention may be used to effect iontophoretic compound transport across any type of tissue, the inventive method is particularly suited for iontophoretic compound transport across skin, mucosa, or eye tissue.

Thus, the invention improves previous known methods for iontophoretically transporting a compound through a localized region of an individual's body tissue wherein a current is applied to the localized region of body tissue through first and second electrodes that are each in contact with the body tissue. The improvement involves measuring the tissue resistance at the first electrode independently from any measurement of tissue resistance at the second electrode, using an iontophoretic reference electrode in combination with either the first or second electrode. This invention can be used to control the resistance at a relatively constant level by a superimposed AC signal. In addition, this invention can adjust other iontophoretic electrical parameters, such as current level or time of administration, based on the electrical resistance measurement at the treatment site. This improved method may be used to improve the precision of iontophoretic extraction of the compound from the body tissue through the localized region, or to improve the precision of iontophoretic delivery of the compound through the localized region into the body tissue.

DETAILED DESCRIPTION OF THE INVENTION

Definitions and Nomenclature

Before describing the present invention in detail, it is to be understood that this invention is not limited to specific drug delivery systems, reverse iontophoresis extraction systems, iontophoresis device structures, sensors, electrode construction designs, barrier-modifying agents, carriers, or the like, as such may vary. It is also to be understood that the terminology used herein is for the purpose of describing particular embodiments only and is not intended to be limiting.

It must be noted that, as used in this specification and the appended claims, the singular forms "a," "an," and "the" include plural referents unless the context clearly dictates otherwise. Thus, for example, reference to "a compound" includes a mixture of two or more compounds as well as a single such compound, reference to "an electrode" includes one or more electrodes, reference to "a sensor" includes a single sensor as well as a combination of sensors, and the like.

In describing and claiming the present invention, the following terminology will be used in accordance with the definitions set out below.

The term "analyte" is used to refer to a compound that is or is to be iontophoretically extracted from an individual's tissue through a localized region. The analyte may be produced by the individual or be introduced into the individual. When particular types of analytes are mentioned, it is to be understood that salts, esters, amides, analogs, conjugates, metabolites, and other derivatives are included unless otherwise indicated.

The terms "barrier-modifying agent" and "barrier modifier" as interchangeably used herein and refer to a compound or composition that is effective to alter the inherent barrier of a body tissue so as to facilitate transport of a compound of interest therethrough. That is, a body tissue such as the skin or mucosa has a barrier that limits the transport of an active agent into or through the body tissue. For example, with skin, the stratum corneum serves as a cutaneous barrier through which most applied compounds and compositions will not penetrate. A barrier-modifying agent, in this context, is a compound that alters the stratum corneum so as to facilitate the transdermal transport of an actively delivered agent or an extracted analyte. Cutaneous barrier modifiers generally disrupt the stratum corneum barrier function by inserting into or otherwise disrupting the lipid bilayer structure in the intercellular regions within the stratum corneum, by inducing hydration and/or swelling of the lipid bilayer, by denaturing epidermal keratin, and/or by facilitating solubilization of the compound to be transported.

The terms "current" and "electrical current," when used to refer to the conductance of electricity by movement of charged particles, are not limited to "direct electrical current," "direct current," or "constant current." The terms "current" or "electrical current" should also be interpreted to include "alternating current," "alternating electrical current," "alternating current with direct current offset," "pulsed alternating current," and "pulsed direct current."

The terms "drug," "active agent," and "pharmacologically active agent" are used interchangeably herein to refer to any chemical compound, complex, or composition that is suitable for topical, transdermal, or transmucosal administration and that has a beneficial biological effect, preferably a therapeutic effect in the treatment of a disease or abnormal physiological condition, although the effect may also be prophylactic in nature. The terms also encompass agents that are administered for nutritive or diagnostic purposes, e.g., nutrients, dietary supplements, and imaging agents. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent," and "drug" are used, then, or when a particular active agent is specifically identified, it is to be understood that applicants intend to include the active agent per se as well as pharmaceutically acceptable, pharmacologically active salts, esters, amides, prodrugs, conjugates, metabolites, analogs, etc.

The term "electrode" is used herein to refer to any terminal that conducts an electric current into or away from a conducting medium. Thus, an iontophoretic electrode is an electrode that conducts an electric current into or away from tissue. When a pure DC signal or AC signal with a DC signal offset is used, the "anode" is the electrode that receives a more positive contribution of the signal, whereas the "cathode" is the electrode that receives a more negative contribution signal. When pure AC is used, there is no formal anode or cathode.

The terms "iontophoresis" and "iontophoretic" are used herein to refer to the transport of a compound through a tissue as a result of an applied electric field. Under the influence of an electric field, certain modifications or alterations of the tissue occur. For example, during and subsequent to conduction of iontophoresis, changes in permeability of the skin may occur due to mechanisms such as the formation of transiently existing pores in the skin (also referred to as "electroporation"). Further, these terms include the transport of one or more compounds by passive, Fickian driven diffusion either concurrent with or subsequent to tissue electroporation by the electrical field. In all cases, the terms generally refer to the transport of one or more compounds through tissue as a result of the application of an electric field, regardless of the mechanism or mechanisms involved.

The terms "optional" and "optionally" mean that the subsequently described circumstance may or may not occur, so that the description includes instances where the circumstance occurs and instances where it does not. For example, recitation of an "optional" DC offset encompasses an iontophoretic process without a DC offset as well as an iontophoretic process with a DC offset.

The term "pore" is used to describe any transport pathway through the tissue, whether endogenous to the tissue or formed by electroporation.

The term "resistance" is used herein in its ordinary sense and refers to the opposition of a body or substance to electrical current passing through it, resulting in a conversion of electrical energy into heat or another form of energy. While the term may be used to describe the opposition of a body or substance to a DC signal, the term "resistance" is also used to refer to its AC analogue, "impedance," which is a measure of the total opposition to current flow in an alternating current circuit, made up of two components— ohmic resistance and reactance. The term "conductance" is also used herein in its ordinary sense and refers to the capacity of a body or substance to conduct electricity, which is measured as the reciprocal of resistance.

As used herein, the term "tissue" refers to an aggregation of similar cells and/or cell components united in performance of a particular function. The term "tissue" may refer to a part of a living organism, a section excised from a living organism, or artificial tissue. Artificial tissue is that within which an aggregation of cells are grown to function similarly to a tissue in a living organism. The aggregated cells, however, are not obtained from a host (i.e., a living organism). Artificial tissues can be grown or cultured in vivo or in vitro. Human skin, for instance, can be cultured in vitro to obtain an aggregation of cells of monolayer thickness or greater that can function as a skin tissue in culture or when grafted onto a living host.

Furthermore, the term "tissue" may refer to human tissue, animal tissue, or sometimes plant tissue cultures. The term may be used in the context of clinical applications for human individuals, as well as veterinary applications and horticultural applications. In the veterinary context, the term may be used to describe any animal having tissues in which pores can be generated via the application of an electrical signal. Hence, some methods can be performed, for example, with domestic animals such as dogs and cats; farm animals such as horses, cows, sheep, and pigs; exotic animals; birds; reptiles; and amphibians; or with tissues from these animals.

The terms "tissue" and "body tissue" are interchangeably used unless the context clearly indicates to the contrary. The term "body tissue" is more typically used herein to refer to tissue from a human individual, e.g., the skin, the mucosal tissue, the ocular surface, etc. Unless otherwise indicated, the term "body surface" is used to refer to skin or mucosal tissue, including the interior surface of body cavities that have a mucosal lining. Unless otherwise indicated, the term "skin" should be interpreted as including "mucosal tissue" and vice versa.

A "localized region" of a tissue refers to the area or section of a tissue that is electroporated via the application of one or more electrical signals and through which a compound of interest is transported. Thus, a localized region of body tissue typically refers to an area of human skin or mucosal tissue through which a compound may be delivered or extracted.

The term "transport," as in the "transport" of a compound of interest across a body tissue, refers to passage of the compound in either direction through the tissue, i.e., the compound may be delivered to the individual from an external source, across the skin or mucosal tissue, or it may be extracted from beneath the individual's body surface, as in analyte extraction.

Iontophoretic Mechanisms and Tissue Resistance Effects

In order to fully elucidate the novelty and nonobviousness of the invention, it should be noted that there are a number of transport mechanisms associated with iontophoresis. Iontophoresis may occur as a result of a direct electrical field effect (e.g., electrophoresis), an indirect electrical field effect (e.g., electroosmosis), electrically induced pore formation (electroporation), or a combination of any of the foregoing. An iontophoretic current is established within an individual's tissue when ions within the tissue are transported as a result of an applied potential. Thus, when iontophoresis occurs as a result of a direct electric-field effect, compounds of interest exhibit either net positive or negative charge. The charged compound is attracted to the electrode of opposite polarity and repulsed by the electrode of similar polarity. As a result, compound transport by this method is directly related to the applied potential and the electrophoretic mobility of the compound. Generally, this mechanism does not affect iontophoretic transport of neutral compounds.

Electroosmosis, on the other hand, is a process whereby an iontophoretic current is generated as the result of movement of ions (primarily $Na^+$ and $Cl^-$) within the tissue to which an iontophoretic current is applied. As a result of this ionic movement, a convective flow is established within a charged pore and the flow conveys any compound dissolved therein. At physiological pH, the pores in the skin carry a negative charge, and positively charged sodium ions carry the bulk of the current through the pores. As a result, when a neutral compound is iontophoretically administered to an individual through the individual's skin, one would expect a higher iontophoretic delivery rate to occur at the anode. Similarly, when a neutral compound, e.g., glucose, is iontophoretically extracted from an individual through the skin, one would expect more compound to be extracted at the cathode than at the anode.

Electroporation of the skin occurs when a sufficiently high electrical current disrupts the lipid bilayers within the stratum corneum, and creates regions of low resistance to both passive and iontophoretically assisted molecular transport. The electrical field disrupts the lipid bilayers within the skin, thus creating zones of low resistance to both passive and iontophoretically assisted molecular transport. The pores created by electroporation provide regions of low resistance to permeation transport through the skin.

Figure 1:
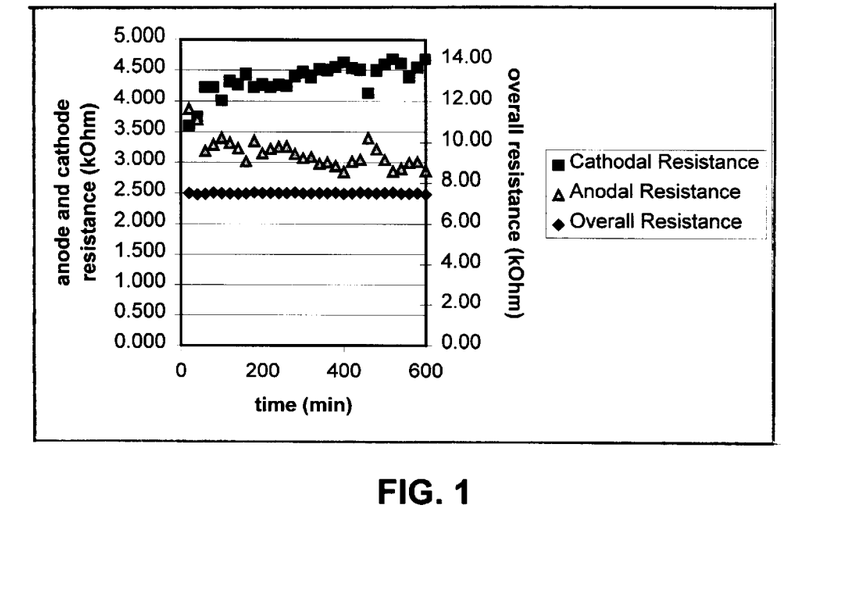
FIG. 1 is a graph that illustrates the distribution of overall resistance between anode and cathode with constant conductance AC iontophoresis having a DC offset.

It has recently been observed that that AC iontophoresis having a DC offset yields results during in vivo constant-conductance iontophoretic glucose extraction that are contrary to the electroosmotic theory as described above. In particular, it has been observed that extraction of glucose at the anode sometimes exceeds extraction from the cathode. To further investigate this phenomenon, a constant conductance iontophoretic experiment was carried out using an AC signal having a DC offset. The resistance of the tissue at the cathode and anode were measured during the experiment and plotted over time in FIG. 1. As illustrated, at the beginning of the experiment, the resistance measured at the anode and the resistance measured at the cathode were approximately equal. As the experiment progressed, the combined resistance at the electrodes was maintained at a constant 7.5 k$\Omega$. However, the resistance at the anode decreased over time, and the resistance at the cathode increased over time. After 600 minutes, the cathodic resistance was equal to about 70% or more of the total resistance. This is contrary to the widely held assumption that the cathode and anode contribute equally to the total resistance associated with iontophoresis. This unexpected result, therefore, demonstrates that there is a need to measure and control the tissue resistance at iontophoretic electrodes independently from each other.

The Inventive Device

Thus, the invention generally provides for monitoring the transport of a compound through a localized region of an individual's body tissue. Unlike previously known monitoring methods that measure the current and/or voltage between the iontophoretic electrodes, the invention employs a novel reference electrode in conjunction with at least one of two iontophoretic electrodes to monitor and control the electrical resistance of the tissue at the localized region. As a result, the resistance at each iontophoretic electrode may be measured independently from the other(s), leading to improved measurement of the electrical resistance at the localized region.

Figure 2:
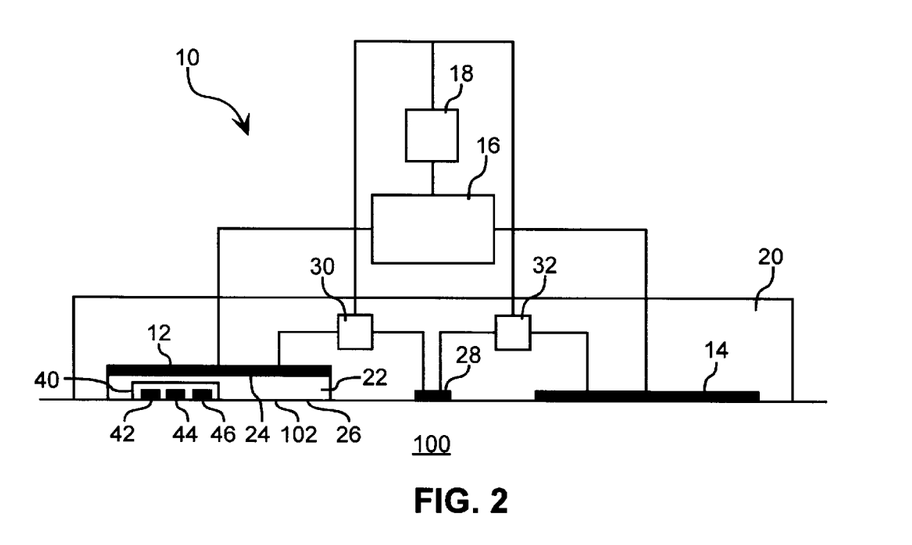
FIG. 2 schematically illustrates an embodiment of the inventive device and the electrical circuitry associated therewith.

FIG. 2 schematically illustrates an embodiment of the inventive device for monitoring iontophoretic transport of a compound. As with all figures referenced herein, in which like parts are referenced by like numerals, FIG. 2 is not to scale, and certain dimensions may be exaggerated for clarity of presentation. As illustrated in FIG. 2, the device 10 generally comprises two iontophoretic electrodes 12 and 14 electrically connected to a current source 16. The first electrode 12 is an active electrode, and the second electrode 14 is a passive electrode. In some instances, however, the second electrode may serve as an additional active electrode.

As shown, both active electrode 12 and inactive electrode 14 are components of an electrode assembly 20 that includes a reservoir 22. Although the reservoir 22 is shown as a cylindrical chamber, the reservoir may take any of a number of forms of varying complexity. In some instances, the reservoir may be as simple as an absorbent pad. Electrode 12 is electrically connected to a reservoir surface 24. Another surface 26 of the reservoir 22 is placed against a localized region 102 of the tissue 100 and held in place, for example, by an adhesive or gel (not shown). As a result, the active electrode 12 is placed in ion-conducting relation with the localized region 102. The inactive electrode 14, immobilized and spaced apart from the active electrode 12, is placed in contact with a surface of the tissue 100 and held in position with an adhesive or gel (not shown). This electrode 14 is positioned to allow for formation of a current that flows between the two electrodes 12 and 14.

The novel reference electrode 28 is also a component of the electrode assembly 20. As such, the reference electrode 28 is immobilized and spaced apart from both the active electrode 12 and the inactive electrode 14. The active electrode 12 and inactive electrodes 14 are each electrically connected to the reference electrode 28 via first and optional second monitoring means, indicated at 30 and 32, respectively. Monitoring means 30 is adapted to measure the voltage difference between the active electrode 12 and the reference electrode 28, and monitoring means 32 is adapted to measure the voltage difference between the inactive electrode 14 and the reference electrode 28

The iontophoretic electrodes 12 and 14, utilized in applying the electrical signals, can be of any of the standard types of electrodes utilized in iontophoresis. Some systems use non-polarizable electrodes, such as standard electrocardiograph electrodes manufactured from silver/silver chloride. Other suitable materials include gold, stainless steel, and platinum. Multichannel dispersive electrodes can also be utilized in certain methods (see, e.g., U.S. Pat. No. 5,415,629). The reference electrode may or may not have a similar construction to the iontophoretic electrodes. It should be noted that as the reference electrode should have surface properties that equal or exceed that of the iontophoretic electrodes, in terms of resistance to formation of interfering layers that may compromise the ability of the monitoring means to accurately monitor the resistance of the localized region.

In operation, the electrodes 12 and 14 are appropriately positioned for iontophoretic compound transport. The first electrode 12 is placed in ion-conducting relation with the localized region, and the second electrode 14 is placed in contact with the individual's body tissue and spaced apart from the first electrode 12. The current source 16 then delivers an electrical signal to electrodes 12 and 14. The particular signals delivered depend on the desired protocols disclosed herein. In some instances, current signals can be delivered for a short time period solely for the purpose of tissue monitoring. While the iontophoretic current is applied, the first monitoring means 30 measures the voltage difference between the active electrode 12 and the reference electrode 28. In addition, the second monitoring means 32 measures the voltage difference between the inactive electrode 14 and the reference electrode 28 during the application of the iontophoretic current.

The size of the region of the tissue to which an iontophoretic current is applied can vary significantly depending upon the nature of the application. In general, the region being electroporated and through which the agent is transported or compound is extracted corresponds to the size of the electrodes 12 and 14, and tends to be from less than about 1 cm$^2$ to greater than about 200 cm$^2$. The size of the region tends to be smaller in other applications, ranging from about 5 cm$^2$ to greater than about 100 cm$^2$. In still other methods, the region tends to be about 5 cm$^2$ to about 30 cm$^2$. The size of the region can also be any particular value within these ranges. The shape of the region can be any geometric shape and is not limited to any one particular shape or type of shape. The design and construction of iontophoretic electrode structures can vary and are discussed in a number of patents and publications. For example, U.S. Pat. No.

6,201,979 to Kumik et al. describes the use of a chemical signal impermeable mask in conjunction with an iontophoretic device. In addition, U.S. Pat. No. 6,259,946 to Higo et al. describes the use of a cup-shaped support in an iontophoresis device that renders the device suitable for mass production at low cost.

The Current Source

As discussed above, the current source 16 is connected to electrodes 12 and 14. The current source may include an alternating current generator, a direct current generator, or both. In some instances, the current source may include an AC generator that may be capable of generating an AC signal having a DC offset. That is, the current source may be a single source capable of delivering both an AC and a DC signal, or it may include two separate sources, one for delivering an AC signal and the other for delivering a DC signal. Thus, the current source 16 may generate a pure AC signal, a pure DC signal, or an AC signal with a DC offset. In some instances, as depicted in FIG. 2, a controller 18 is also provided in electrical communication with electrodes 12 and 14 and the current source 16.

In some instances, AC signals, i.e., electrical currents that reverse direction periodically, are preferred over purely DC signals for use in the present invention. The applied AC signal is of an appropriate voltage and waveform to effectively induce and/or maintain a desired electrical state. Typically, the desired tissue state is an electroporated state that allows for enhanced transport of the agent relative to untreated tissue. Typically, the target electrical state is a selected electrical resistance or electrical conductance. Typically, the AC signal is applied to maintain the substantially constant electrical state throughout the time period during which transport of agent occurs. The actual period for compound delivery or extraction depends upon the nature of the application. Some applications can be performed in less than 10 minutes, while other applications may last 12 hours to 24 hours or more.

The frequency, waveform, and duration of the AC signal can vary as long as it is effective to maintain the selected electrical state within the desired range. The frequency of the current waveform may be variable but is preferably constant. Typically, the AC signal has a frequency of at least about 1 Hz. In certain methods, the applied frequency generally falls within the range of about 1 Hz to about 1 kHz; while in other methods, the frequency usually is within the range of about 1 kHz to about 10 kHz. In yet other methods, the frequency usually is within the range of 10 kHz to 30 kHz, or 30 kHz to 200 kHz. The actual frequency can be any particular value or range of values within these ranges. A variety of waveforms can be utilized. Suitable waveforms include both symmetric and asymmetric waveforms, including waveforms having square, triangular, sinusoidal, sawtooth, trapezoidal shapes, and the like. It should be noted that the term "AC signal" refers not only to signals that reverse direction relative to a zero reference point, but also to signals that are biased relative to a zero reference point; thus, AC signals having a DC offset may be employed with the invention as well.

The Monitoring Means

As discussed above, the inventive device may include one or more monitoring means. As depicted in FIG. 2, the active electrode 12 and inactive electrode 14 are each electrically connected to the reference electrode 28 via first and optional second monitoring means, indicated at 30 and 32, respectively. The monitoring means usually has a high electrical resistance compared with the resistance of the reference electrode and the tissue in electrical contact with the electrode. Monitoring means 30 is adapted to measure the voltage difference between the active electrode 12 and the reference electrode 28, and monitoring means 32 is adapted to measure the voltage difference between the inactive electrode 14 and the reference electrode 28. Either or both monitoring means 28 and 30 may be adapted to continuously monitor the electrical resistance of the localized region. In the alternative, the monitoring means may be adapted to intermittently monitor the electrical resistance of the localized region. In such a case, intermittent monitoring may occur at predetermined intervals. Such intervals may occur at a constant frequency, increasing frequency, decreasing frequency, or a combination thereof. Optimally, the monitoring means is adapted to monitor the electrical resistance of the localized region at intervals selected according to the current applied by the current source.

The use of such a monitoring means provides a number of advantages previously unknown in the art. For example, U.S. patent application Ser. No. 10/014,741, entitled "Method for Increasing the Battery Life of an Alternating Current Iontophoresis Device Using a Barrier Modifying Agent," filed Dec. 10, 2001, by inventors Miller, Higuchi, Li and Flynn, employs a set of electrodes in addition to iontophoretic electrodes to monitor the resistance at the iontophoretic transport site. In contrast, the monitoring means of the present invention may be directly connected to the active iontophoretic electrode. Thus, the monitoring means of present invention provides at least two advantages over that described in U.S. patent application Ser. No. 10/014,741. First, in previous simultaneous and independant efforts to carry out iontophoresis and to measure the electrical resistance at a tissue site, at least four electrodes are used—two iontophoretic electrodes to bring about iontophoresis and two additional electrodes, or "monitoring" electrodes, to monitor tissue resistance. The monitoring means is electrically connected to the two monitoring electrodes. In the present invention, however, at least one electrode used to effect iontophoresis is also electrically connected to the monitoring means. That is, at least one electrode serves as both an iontophoresis electrode and a monitoring electrode. Thus, a monitoring electrode may be eliminated. In addition, since the electrical resistance at both the active and inactive electrode sites can be monitored independently, a more accurate measurement of the resistance of tissue at the iontophoretic transport site is obtained than by those means that do not directly measure the resistance at each site independently. Furthermore, the monitoring means, as discussed below, further represents a component of a feedback mechanism that allows the controller to tailor the application of iontophoretic current to the localized region. However, even in instances wherein a feedback mechanism is not used, the monitoring means may allow for corrections in transport data.

The Controller

As discussed above, the inventive device depicted in FIG. 2 includes an optional controller 18, such as one that employs microprocessor control technology. Typically, the controller 18 is adapted to control the iontophoretic current applied to the localized region. In some instances, the controller may be programmed to deliver predetermined signals to the localized region 102, regardless of the measurements made by either or both of the monitoring means 30 and 32. In other instances, the monitoring means 30 and 32 are each connected to the optional controller 18 in a manner sufficient to communicate the measured voltage difference between the iontophoretic electrodes 12 and 14 and the reference electrode 28. In such a case, the controller 18 may be adapted to control the current applied to the localized region 102 according to the electrical resistance of the localized region 102 monitored by either or both of monitoring means 30 or 32. For example, the controller 18 may be adapted to control the current applied to the localized region to maintain the electrical resistance of the localized region within a resistance range. Such a resistance range may be predetermined. Typically, the controller 18 is adapted to maintain the electrical resistance between the first and reference electrodes at a constant value. Accordingly, if during the transport process, the resistance of the localized region 102 drifts outside of a predetermined range, this deviation should be detected through the use of the reference electrode 28 and either or both of monitoring means 30 and 32. The monitoring means 30 and 32 may then communicate with the controller 18, which, in turn, makes appropriate adjustments such that the current source 16 varies the iontophoretic voltage applied and allows the electrical resistance at the localized region 102 to be brought back within the resistance range.

The controller may vary the iontophoretic signal as needed to maintain the electrical resistance of the localized region at a constant value, or more typically, within a range. For methods in which electrical resistance of an individual's skin is monitored, the resistance of the localized region may vary somewhat from individual to individual. In general, however, the resistance tends to be approximately 1–30 $k\Omega/cm^2$, and more typically, within the range of approximately 5–15 $k\Omega/cm^2$. The iontophoretic voltage is typically applied as necessary to maintain the tissue resistance at a level that does not increase or decrease by more than about 20% of a predetermined value. Thus, if the value is 5 $k\Omega/cm^2$, then the iontophoretic signal is varied as required to keep the measured resistance within the range of about 4–6 $k\Omega/cm^2$. In certain other methods, the fluctuation is limited to less than 10% of the target value; in other methods, less than about 5%; and in still other methods, less than about 1%.

The controller may also vary the iontophoretic signal as needed for other purposes. For example, the controller may be employed to alter the current to control the rate of compound transport based on the resistance of the target area. Secondly, the controller may be employed to alter the time of iontophoretic permeant transport based on the resistance of the target site. In addition, the controller may be used to lessen or minimize tissue irritation during compound transport. Optionally, such a controller can also include a safety shut off if it is determined that the electrical state of an individual's tissue has become unacceptable.

As discussed above, AC iontophoretic signals are preferred over purely DC signals. When an AC signal is employed, the controller may vary the amplitude and/or frequency of the applied voltage as needed. Thus, in some instances, the waveform of the signal may be varied. Similarly, when an AC iontophoretic signal with a DC offset is employed, the controller may increase or decrease the magnitude of DC offset as well as the relative contributions of the AC and DC components of the iontophoretic signal.

As discussed in International Patent Publication Nos. WO 01/60448 and WO 01/60449, a relatively high-voltage DC or AC prepulse can optionally be applied to the body tissue to quickly attain a target electrical state or state of electroporation, which is subsequently maintained by adjusting the AC signal. The advantage of using a prepulse is that it can accelerate the process of establishing a desired electrical state of the localized tissue region. Once the prepulse elicits the desired electrical state, the flux of the compound being transported through the localized region can be regulated by controlling the iontophoretic current, as described above.

In general, the characteristics of the AC or DC prepulse are selected to be effective to obtain the desired electrical state. Typically, this means that the prepulse signal is applied to reach a target electrical resistance or conductance. In the absence of a barrier-modifying agent, the required voltage of the prepulse could be as high as 90 V. If an AC prepulse is utilized, the AC prepulse can be symmetric or asymmetric. A variety of suitable AC prepulse waveforms can be used, including, but not limited to, a square waveform, a sinusoidal waveform, a saw-tooth waveform, or a trapezoidal waveform. The duration of the prepulse is sufficiently long so as to achieve the desired electrical state. Duration of the prepulse depends in part upon the voltage of the prepulse. In general, however, the prepulse is typically from less than 1 minute to more than 100 minutes. If a DC prepulse is utilized, it also can be supplied in a variety of waveforms wherein the shape is square, triangular, trapezoidal, or saw-tooth, for example. As with an AC prepulse, the DC prepulse is of sufficient duration to establish the target electrical state.

The controller may apply a DC offset signal simultaneously with application of the AC signal. This timing is appropriate, for example, when a prepulse has already established the desired electrical state. In other methods, however, the DC offset signal is delayed until after the AC signal has been initiated. A delay may be appropriate, for instance, with methods conducted without a prepulse to allow the AC signal to establish the target electrical state. Normally, the voltage of the DC offset signal is in the range of about 0.1 V to about 5 V, while in other methods the voltage is in the range of about 0.1 to about 2.5 V. The current range typically is about 0.01 to about 0.5 $mA/cm^2$.

Iontophoretic Delivery

The inventive device may be used to effect iontophoretic compound delivery through the localized region. When compound delivery is desired, reservoir 22 houses at least one compound to be transported through the localized region into, and optionally through, the individual's body tissue. Typically, the compound is a pharmacologically active agent that can be iontophoretically transported across tissue. In general, a pharmacologically active agent that will be iontophoretically administered using the present method will be selected from the classes of active agents provided in U.S. patent application Ser. No. 10/014,741. In some instances, two or more pharmacologically active agents are administered in combination. Further, a pharmacologically active agent can be combined with various agents that enhance certain aspects of transport. For instance, a first active agent can be combined with a second active agent that improves blood circulation, to consequently enhance the rate of delivery of the therapeutic agent throughout an individual's body. In some instances, one or more excipients acting to control the level of transport that occurs during the procedure may be utilized.

The active agent will generally be delivered as a component of a pharmaceutical formulation suitable for topical, transdermal, transmucosal, and/or transoccular administration, and will contain at least one pharmaceutically acceptable vehicle. Examples of vehicles typically used in such formulations are distilled water, buffered water, physiological saline, PBS, Ringer's solution, dextrose solution, and Hank's solution. In addition, the formulation can include other carriers, adjuvants, and/or non-toxic, non-therapeutic, nonimmunogenic stabilizers, excipients, and the like. The formulation may also include additional substances to approximate physiological conditions, such as pH-adjusting and -buffering agents, tonicity-adjusting agents, wetting agents, detergents, and the like. Further guidance regarding formulations that are suitable for various types of administration can be found in *Remington's Pharmaceutical Sciences*, Mack Publishing Company, Philadelphia, Pa., 17th ed. (1995).

The pharmacologically active agent suitable for use with the invention is typically administered in an amount effective for prophylactic and/or therapeutic purposes. An effective therapeutic amount is an amount sufficient to remedy a disease state or symptoms, or otherwise prevent, hinder, retard, or reverse the progression of a disease or any other undesirable symptoms. An effective prophylactic amount is an amount sufficient to prevent, hinder, or retard a disease or any other undesirable symptom. The effective amount of any particular active agent will depend upon a number of factors known to those of skill in the art, including, for example, the potency and potential toxicity of the agent, the stability of the agent in the body, and the age and weight of the individual.

The active agents can also be compounds that are not delivered for a therapeutic or prophylactic purpose, but that are otherwise physiologically or medically useful. Such compounds include, by way of example, nutrients and imaging agents.

Iontophoretic Extraction

Similarly, the inventive device may be used to effect iontophoretic compound extraction through the localized region. When compound extraction is desired, reservoir 22 is designed and constructed to receive, collect, and contain one or more analytes that are extracted through the localized region. The analyte may be any substance that is in the system or body (e.g., circulatory system or tissue system) of an individual and that can be transported across an electroporated tissue. When the tissue is human skin, the substance is either endogenous or one that has previously been introduced into the body by some outside means. Thus, the extracted compounds, i.e., the analytes, can be molecular entities that are markers of disease states, markers of the physiological states of the tissues, pharmacologically active agents that have been administered to the subject, metabolites of such pharmacologically active agents, substances of abuse, electrolytes, minerals, hormones, peptides, metal ions, nucleic acids, genes, or enzymes, or any metabolites, conjugates, prodrugs, analogs, or other derivatives of the aforementioned substances. In some instances, more than one analyte of monitoring interest may be extracted at a time. The substances can be charged (negatively or positively), uncharged, or electronically neutral (e.g., zwitterionic substances with an equal number of opposite charges).

Substances that can be monitored further include, but are not limited to, oligosaccharides, monosaccharides (e.g., glucose), various organic acids (e.g., pyruvic acid and lactic acid), alcohols, fatty acids, cholesterol and cholesterol-based compounds, and amino acids. A number of different analytes that correlate with particular diseases or disease states can be monitored. For example, phenylalanine levels can be ascertained to monitor the treatment of phenylketonuria, a condition that is manifested by elevated blood phenylalanine levels. Examples of metal analytes that can be monitored include, but are not limited to, calcium, zinc, iron, copper, magnesium, and potassium. Additional analytes that can be extracted from humans are discussed in "Iontophoresis Devices for Drug Delivery," by Praveen Tyle, Pharmaceutical Research, vol. 3, no. 6, pp. 318–326. Similarly, the concentration may be measured of various pharmacologically active agents that have been administered for either therapeutic or prophylactic treatment. Examples of such substances are described in U.S. patent application Ser. No. 10/014,741.

Once extracted, the analyte may be analyzed using any of a number of analytical tools known in the art. For example, if a liquid is collected within the reservoir, the collected liquid may be analyzed for the presence, quantity, or concentration of one or more compounds of interest using chromatographic methods (e.g., high performance liquid chromatography), spectroscopic methods (e.g., infrared spectroscopy, nuclear magnetic resonance spectroscopy, and/or mass spectrometry), electrochemical methods (e.g., electrical resistance and/or electrical potential), and enzymatic methods coupled with colorimetric analysis or electrical potential changes. Combinations of analytical techniques can also be utilized (e.g., gas chromatography/mass spectrometry). Detection of the substance can be either qualitative or quantitative.

The Sensor

The inventive device may include a sensor 40, as depicted in FIG. 2, for measuring the quantity and/or concentration of the compound in the reservoir. Such a sensor can be used to monitor the progress of the iontophoretic delivery or extraction carried out by the iontophoretic electrodes. For iontophoretic delivery, the sensor may be used to monitor the amount of compound to be transported that remains in the reservoir. For iontophoretic extraction, the sensor may be used to monitor the quantity of fluids extracted as well as to determine the proportion of different compounds extracted.

For iontophoretic extraction, a number of electrochemical sensors are known in the art. See, e.g., U.S. Pat. No. 6,144,869 to Berner et al. Such sensors 40 include at least one working electrode 42 and a counter electrode 44. The working electrode serves to monitor or determine the amount of electrical signal at a point in time or over a given time period. The signal may then be correlated with the concentration of a chemical compound.

Typically, the working electrode has a reactive surface that converts contact with the analyte to an electrical signal. The reactive surface can be comprised of any electrically conductive material such as, but not limited to, platinum-group metals (including platinum, palladium, rhodium, ruthenium, osmium, and iridium), nickel, copper, silver, and carbon, as well as oxides, combinations, or alloys thereof. In some instances, an enzyme can be contained in the reservoir. The enzyme may be selected to catalyze a reaction with the extracted analyte, e.g., glucose, to the extent that a product of this reaction can be sensed. For example, glucose oxidase is an enzyme that oxidizes glucose to gluconic acid and hydrogen peroxide. The working electrode may serve to electrochemically reduce the hydrogen peroxide molecule. As a result, e.g., two electrons are generated for each hydrogen peroxide molecule. By measuring the current generated, the amount of glucose entering the reservoir may be monitored. Glucose oxidase (GOx) is readily available commercially and has well known catalytic characteristics. However, other enzymes can also be used, so long as they specifically catalyze a reaction with an analyte or substance of interest to generate a detectable product in proportion to the amount of analyte so reacted.

Similarly, a number of other analyte-specific enzyme systems can be used in the invention. For example, a biosensor electrode that detects hydrogen peroxide can be used to detect ethanol using an alcohol oxidase enzyme system, or similarly, uric acid with urate oxidase system, urea with a urease system, cholesterol with a cholesterol oxidase system, and theophylline with a xanthine oxidase system. In addition, the oxidase enzyme (used for hydrogen peroxide-based detection) can be replaced with another redox system, for example, the dehydrogenase enzyme NAD-NADH, which offers a separate route for detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine, triglycerides, and urea. Further, the enzyme can be eliminated, and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, hydrogen ions (pH), potassium, sodium, and urea. Also, the sampling system described herein can be used for therapeutic drug monitoring, for example, to monitor anti-epileptic drugs (e.g., phenytion), chemotherapy (e.g., adriamycin), hyperactivity (e.g., methylphenidate), and anti-organ-rejection (e.g., cyclosporin).

In these electrochemical sensors, the counter electrode 44 serves to complete an electrical circuit through which the electrical signal may be transmitted. In some instances, the counter electrode also serves as a reference electrode for the sensor. In other instances, an additional electrode is provided as a reference electrode 46. It should be noted that the term "reference electrode" is used differently in the context of sensors than in the context of monitors for the electrical resistance of the localized region. The sensor reference electrode may be, but is typically not, in electrical communication with the monitoring means. The reference electrode used to monitor the electrical resistance of the localized region must be in electrical communication with the monitoring means. In any case, electrochemical sensors may be adapted to carry out analyte analysis through techniques such as amperometry, coulometry, and/or potentiometry.

In addition or in the alternative, the sensor may use optical technologies. For example, the reservoir can include various agents that specifically react with one or more compounds of interest to form a detectable product or complex. For example, the reservoir can include a dye that emits or absorbs light of a particular wavelength upon interaction with a particular compound. Such alteration in light may be detected through optical sensors known in the art.

Additional Barrier-Modifying Techniques

Optionally, additional barrier-modifying techniques may be used in conjunction with the present invention. Such techniques may be chemical or mechanical in nature and are effective to alter the inherent barrier characteristics of a body tissue so as to facilitate transport of a compound of interest therethrough. For example, such techniques may involve the application of ultrasonic energy, heat, radiation (e.g., through laser ablation, or otherwise), and/or mechanical abrasion that may result in selective tissue removal. Such techniques may also involve the application of a barrier-modifying agent. As discussed in U.S. patent application Ser. No. 10/014,741, application of a barrier-modifying agent, either prior to, during, or both prior to and during application of the AC signal, has now been found to be effective in decreasing the amount of current and/or electrical potential required to achieve and sustain electroporation. Decreasing the required current and/or potential not only reduces patient discomfort, but also extends battery life in iontophoretic devices. In addition, the presence of the barrier-modifying agent enables a lower level of current and/or voltage to achieve the desired electrical state, for both the AC signal and the optional prepulse, as the barrier-modifying agent reduces the electrical potential needed to lower the resistance of the tissue to a target resistance.

Thus, a barrier-modifying agent may be used in conjunction with the invention. While barrier-modifying agents may theoretically serve to increase or decrease the permeability of the tissues to one or more compounds, those suitable for use for the present invention should increase the permeability of the tissue with respect to at least one compound or have a favorable effect on the electrical parameters needed to extract the compound or compounds of interest. The barrier-modifying agent may increase the permeability of the tissue to all or to selected compounds. When the invention is used to effect iontophoresis in dermal tissue, suitable barrier modifiers will generally, although not necessarily, be modifiers of the cutaneous barrier, wherein permeability of the outer layer of the skin can be enhanced in at least one of several ways. That is, the barrier modifiers may act as lipid bilayer disrupting agents by inserting into or otherwise disrupting the bilayer structure in the intercellular spaces of the stratum corneum. Other barrier modifiers may cause hydration and/or swelling of the lipid bilayer, changing the pore charge density or pore size, thereby facilitating passage of certain types of compounds. Still other barrier modifiers may alter the helical keratinous filaments of the stratum corneum, as thought to be the case with certain anionic surfactants. Any or all of these barrier modifiers may also facilitate solubilization of the transported molecule, which in turn promotes transport through the body tissues. The barrier-modifying agent may be applied to the body tissue prior to, during, or both prior to and during application of the iontophoretic electrical signal. If administered prior to iontophoresis, the barrier-modifying agent may be applied alone or in a suitable carrier system. If the barrier modifier is to be administered concurrently with iontophoresis, the agent may be contained within the iontophoretic device.

In general, the chemical barrier-modifying agent may be selected from those known the art, e.g., from the following groups: fatty acids; fatty alcohols; bile acids; bile salts; nonionic surfactants; anionic surfactants; cationic surfactants; amphoteric surfactants; hydrocarbon solvents; esters; amides; pyrrolidones; sulfoxides; cyclodextrins; alkyl N,N-disubstituted amino esters; N-alkyl-azacycloalkanones and N-alkyl-azacycloalkenones; terpenes; and urea and its derivatives. Additional details relating to these barrier-modifying agents can be found in U.S. patent application Ser. No. 10/014,741. Barrier-modifying agents are typically used in the formulation delivered to the skin in the range of approximately 0.1 to 50%, more preferably in the range of approximately 0.5 to 40%, and most preferably in the range of approximately 1.0 to 10% (v/v). Similarly, the inventive device may include additional means, chemical, mechanical or otherwise, for carrying out the above-described barrier modifying techniques.

Variations of the invention, not explicitly disclosed herein, will be apparent to those of ordinary skill in the art. For example, it is generally preferred that all iontophoretic electrodes used herein are place in ion-conducting relation with the body tissue. As another example, through the use of solid-state circuitry, the various foregoing elements such as the electrodes, current source, and reservoir can be included in a small, integrated device that can be conveniently worn by an individual without interfering with the individual's daily activities. Similarly, an on-board CPU may be used to analyze the resistance data at the transport site and correct the iontophoretic current output to adapt to changes in membrane permeability.

It is to be understood that while the invention has been described in conjunction with the preferred specific embodiments thereof, the foregoing description, as well as the example that follows, are intended to illustrate and not limit the scope of the invention. Other aspects, advantages, and modifications will be apparent to those skilled in the art to which the invention pertains. All patents, patent applications, journal articles, and other references cited herein are incorporated by reference in their entireties.

EXAMPLE

Figure 3:
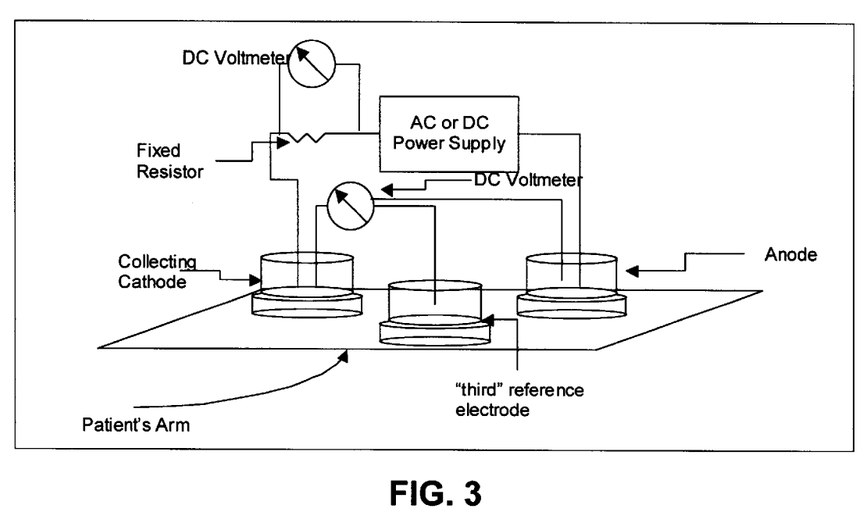
FIG. 3 schematically illustrates another embodiment of the inventive device that was used to demonstrate the use of a reference electrode in conjunction with an AC iontophoresis signal having a DC offset to maintain the electrical resistance of a localized region of an individual's tissue at a constant level FIGS. 4A and 4B, collectively referred to as FIG. 4, illustrate the results of experiments using the device illustrated in FIG. 3 to maintain constant cathodal resistance during extractive iontophoresis.

The device depicted in FIG. 3 was used to carry out extractive iontophoresis using an AC signal with a DC offset. The electrodes were prepared using silver foil obtained from EM Science (Gibbstown, N.J.). The silver foil was cleaned with steel wool and was then dipped in a 50% (w/w) mixture of liquid silver paint purchased from Ladd Research (Williston, Vt.) and finely ground AgCl from Sigma Chemical (St. Louis, Mo.). The AgCl-coated silver foil strips were allowed to cure overnight at room temperature.

The top half of a Franz type diffusion cell was adhered to a volunteer's skin with a suitable pressure-sensitive adhesive (3M part number 051131-06439, St. Paul, Minn.) to each of three electrode positions on the individual's forearm in a tight triangular configuration. Each electrode chamber was filled with 1.5 mL of phosphate buffered saline, pH 7.4 (PBS; from Sigma Chemical, St. Louis, Mo.). The first and second electrode chambers each contained two electrodes, one of which was connected to the current generator, and the second (the sensing electrode), to a Fluke Multimeter™ for resistance determination. The first electrodes are termed the working electrodes and the second electrodes are termed the sensing electrodes. The third electrode chamber contained only a sensing electrode.

The voltage at each site was calculated using equation (I) as follows:

$$R_a = \frac{V_{3 \to a}}{I_{skin}} \quad (I)$$

where $R_a$=resistance at site a $V_{3 \to a}$=Voltage from reference position (3$^{rd}$ electrode) to site a $I_{skin}$=current across skin (from site a to b).

Since the current across the skin is the same as the current across a fixed resistor, equation (II) describes the relationship between the electrical resistance across the volunteer's skin, $R_{skin}$ and that of the resistor:

$$R_{skin} = \frac{V_{skin}}{V_{resistor}} * R_{fixed\ resistor} \quad (II)$$

where $V_{skin}$=voltage measured across sites a and b $V_{resistor}$=voltage measured across fixed resistor $R_{fixed\ resistor}$=resistance value of fixed resistor.

The current passed across the volunteer's skin, ($I_{skin}$) through the first and second electrode chamber can be calculated as:

$$I_{skin} = \frac{V_{skin}}{R_{skin}} = \frac{V_{skin}}{\frac{V_{skin} * R_{fixed\ resistor}}{V_{resistor}}} = \frac{V_{skin} * V_{resistor}}{V_{skin} * R_{fixed\ resistor}} = \frac{V_{resistor}}{R_{fixed\ resistor}} \quad (III)$$

A custom-built, precision function current source from EM-Tech Electronics (Lindon, Utah) was used to supply an AC current through the anode and cathode such that a voltage difference was generated across the 7.5 kΩ fixed resistor. Simultaneously, a constant DC offset current of 0.2 mA was maintained by the current source. The resistance at the cathode site was maintained by adjusting the AC potential. If the resistance at the cathode site drifted higher than the 3.75 kΩ target, the magnitude of the applied AC potential was increased to augment the degree of electroporation of the skin and lower the resistance of the area to the target value. If the resistance dropped below the target value, the AC voltage was lowered and the amount of electroporation allowed to recover.

Figure 4A:
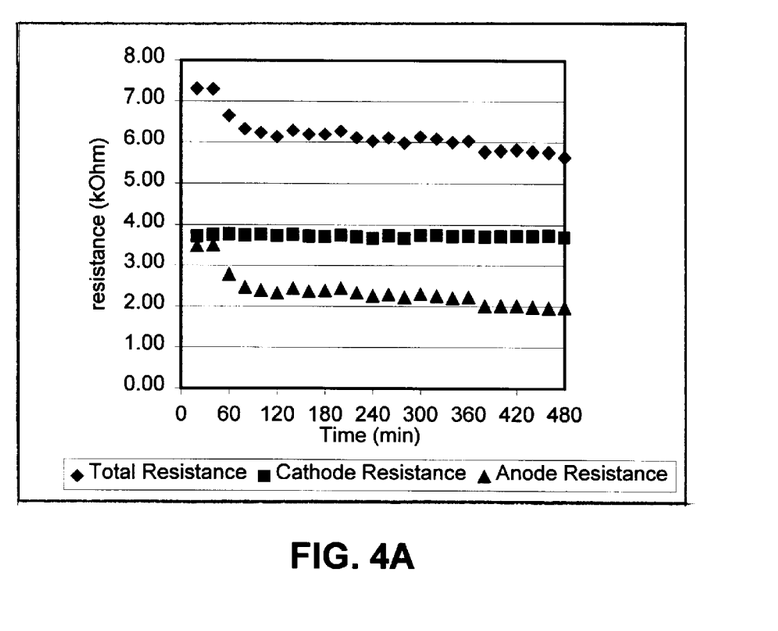
Figure 4B:
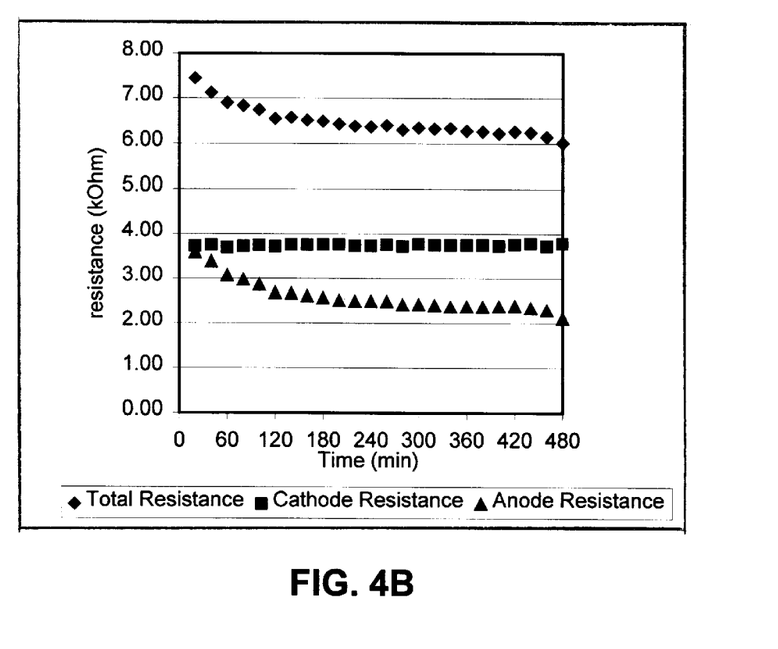

The experiment was carried out twice. The results are graphically illustrated in FIG. 4. Despite a continually decaying anodal resistance, the cathodal resistance remained constant (with±0.5%) throughout the entirety of each eight-hour experiment. That is, the resistance at the cathode was maintained at 3.75 kΩ within very tight tolerances (average 3.74±0.02 kΩ). Thus, tight control of the electrical resistance was demonstrated at the cathode site despite the overall deterioration in the anodal resistance, and therefore in the overall resistance. In these particular examples, the cathode sites were chosen because the experiments studied glucose extraction. Although this example is specific for maintaining the cathode resistance during analyte extraction, it is not limiting. This same invention can be used to control cathodal or anodal resistance during both analyte extraction and drug delivery.

We claim:

1. A device for iontophoretically transporting a compound through a localized region of an individual's body tissue, comprising:

a first electrode adapted to be placed in ion-conducting relation with the localized region to allow iontophoretic transport of a compound therethrough;

a second electrode adapted to contact the individual's body tissue and spaced apart from the first electrode;

a reference electrode adapted to contact the individual's body tissue and spaced apart from the first and second electrodes;

a current source electrically connected to the first and second electrodes, for applying a current to the localized region of body tissue to transport the compound iontophoretically through the localized region; and a monitoring means for monitoring the electrical resistance of the localized region by measuring any voltage difference between the reference electrode and at least one of the first and second electrodes.

2. The device of claim 1, further comprising a controller for controlling the current applied to the localized region of body tissue by the current source.

3. The device of claim 2, wherein the controller is adapted to control the current applied to the localized region according the electrical resistance of the localized region monitored by the monitoring means.

4. The device of claim 2, wherein the controller is adapted to control the duration of current applied to the located region of body tissue by the current source.

5. The device of claim 4, where the controller is adapted to control the duration of current applied according to the electrical resistance of the localized region monitored by the monitoring means.

6. The device of claim 1, further comprising a controller for controlling the electrical potential applied to the localized region so as to maintain the electrical resistance of the localized region within a resistance range.

7. The device of claim 6, wherein the resistance range is predetermined.

8. The device of claim 7, wherein the controller is adapted to maintain the electrical resistance between the first and reference electrodes at a constant value.

9. The device of claim 1, wherein the monitoring means is adapted to measure any voltage difference between the reference electrode and the first electrode.

10. The device of claim 1, wherein the monitoring means is adapted to measure any voltage difference between the reference electrode and the second electrode.

11. The device of claim 1, wherein the second electrode is adapted to be placed in ion-conducting relation with the body tissue.

12. The device of claim 1, wherein the reference electrode is immobilized with respect to at least one of the first and second electrodes.

13. The device of claim 1, wherein the first electrode is a component of an electrode assembly adapted to deliver a compound through the localized region.

14. The device of claim 13, wherein the assembly comprises a reservoir housing a compound to be transported through the localized region into and optionally through the individual's body tissue.

15. The device of claim 14, wherein the compound is a pharmacologically active agent.

16. The device of claim 1, wherein the first electrode is a component of an electrode assembly adapted to receive a compound transported through the localized region.

17. The device of claim 16, wherein the assembly comprises a reservoir for collecting and containing a compound extracted from the individual's body tissue.

18. The device of either claim 13 or claim 16, further comprising a sensor for measuring the quantity and/or concentration of the compound in the reservoir.

19. The device of claim 18, wherein the sensor is an electrochemical sensor comprising a working electrode and a counter electrode.

20. The device of claim 19, wherein the sensor further comprises a sensor reference electrode.

21. The device of claim 18, wherein the sensor is an optical sensor.

22. The device of claim 18, wherein the sensor is a coulometric or amperometric sensor.

23. The device of claim 18, wherein the sensor is a potentiometric sensor.

24. The device of either claim 13 or claim 16, wherein the assembly further comprises a barrier-modifying agent for delivery to the localized region.

25. The device of claim 24, wherein the barrier-modifying agent enhances compound transport through the localized region.

26. The device of claim 1, wherein the current source comprises an alternating current generator.

27. The device of claim 26, wherein the alternating current generator is capable of generating an alternating current having a direct current offset.

28. The device of claim 1, wherein the current source comprises a direct current generator.

29. The device of claim 1, wherein the monitoring means is adapted to continuously monitor the electrical resistance of the localized region.

30. The device of claim 1, wherein the monitoring means is adapted to intermittently monitor the electrical resistance of the localized region.

31. The device of claim 30, wherein the monitoring means is adapted to intermittently monitor the electrical resistance of the localized region at predetermined intervals.

32. The device of claim 31, wherein the predetermined intervals occur at a constant frequency.

33. The device of claim 31, wherein the predetermined intervals occur at an increasing frequency.

34. The device of claim 31, wherein the predetermined intervals occur at a decreasing frequency.

35. The device of claim 30, wherein the monitoring means is adapted to monitor the electrical resistance of the localized region at intervals selected according to the current applied by the current source.

36. A method for iontophoretically transporting a compound through a localized region of an individual's body tissue, comprising:
   (a) placing a first electrode in ion-conducting relation with the localized region;
   (b) placing second and reference electrodes in contact with the individual's body tissue, wherein the electrodes are spaced apart from each other;
   (c) applying a current to the localized region of body tissue through the first and second electrodes to transport a compound iontophoretically through the localized region; and
   (d) monitoring the electrical resistance of the localized region during step (c) by measuring any voltage difference between the reference electrode and at least one of the first and second electrodes.

37. The method of claim 36, wherein the current applied in step (c) is controlled by the electrical resistance monitored in step (d).

38. The method of claim 37, wherein step (d) is carried out intermittently.

39. The method of claim 38, wherein step (d) is carried out intermittently at predetermined intervals.

40. The method of claim 39, wherein the predetermined intervals occur at a constant frequency.

41. The method of claim 39, wherein the predetermined intervals occur at an increasing frequency.

42. The method of claim 39, wherein the predetermined intervals occur at a decreasing frequency.

43. The method of claim 39, wherein step (d) is carried out at intervals selected according to the current applied in step (c).

44. The method of claim 36, wherein the duration of step (c) is controlled by the electrical resistance monitored in step (d).

45. The method of claim 36, wherein the electrical resistance of the localized region is maintained within a resistance range.

46. The method of claim 45, wherein the resistance range is predetermined.

47. The method of claim 46, wherein the electrical resistance between the first and reference electrodes is maintained at a constant value.

48. The method of claim 36, wherein the body tissue is skin.

49. The method of claim 36, wherein the body tissue is mucosal tissue.

50. The method of claim 36, wherein the body tissue is eye tissue.

51. The method of claim 36, wherein the current is an alternating current.

52. The method of claim 51, wherein the alternating current has a direct current offset.

53. The method of claim 36, wherein the current is a direct current.

54. The method of claim 36, wherein step (c) comprises iontophoretically delivering a compound from a reservoir through the localized region into the individual's body tissue.

55. The method of claim 36, wherein step (c) comprises iontophoretically extracting a compound from an individual's body tissue through the localized region.

56. The method of claim 36, wherein step (d) comprises measuring any voltage difference between the reference electrode and the first electrode.

57. The method of claim 36, wherein step (d) comprises measuring any voltage difference between the reference electrode and the second electrode.

58. The method of claim 36, wherein step (d) is carried out continuously.

59. In a method for transporting a compound iontophoretically through a localized region of an individual's body tissue wherein a current is applied to the localized region of body tissue through first and second electrodes each in contact with the body tissue, the improvement comprising measuring the tissue resistance at the first electrode independently from tissue resistance at the second electrode, using an iontophoretic reference electrode in combination with either the first or second electrodes.

60. The method of claim 59, wherein the method comprises extracting the compound from the body tissue through the localized region.

61. The method of claim 59, wherein the method comprises delivering the compound through the localized region into the body tissue.

62. The method of claim 59, wherein the current is a direct current.

63. The method of claim 59, wherein the current is an alternating current.

64. The method of claim 63, wherein the alternating current has a direct current offset.

* * * * *